(12) United States Patent
Akil et al.

(10) Patent No.: US 10,392,435 B2
(45) Date of Patent: Aug. 27, 2019

(54) METHOD FOR DECREASING DEPRESSION-LIKE BEHAVIOR WITH CONNECTIVE TISSUE GROWTH FACTOR (CTGF) INHIBITOR

(71) Applicant: The Board of Trustees of the Leland Stanford Junior University, Stanford, CA (US)

(72) Inventors: Huda Akil, Ann Arbor, MI (US); Stanley Watson, Ann Arbor, MI (US); Cortney Turner, Willis, MI (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/833,273

(22) Filed: Dec. 6, 2017

(65) Prior Publication Data
US 2018/0208649 A1    Jul. 26, 2018

Related U.S. Application Data

(63) Continuation of application No. PCT/US2016/037415, filed on Jun. 14, 2016.

(60) Provisional application No. 62/175,828, filed on Jun. 15, 2015.

(51) Int. Cl.
| | |
|---|---|
| *A61K 38/18* | (2006.01) |
| *A61K 39/00* | (2006.01) |
| *A61P 25/24* | (2006.01) |
| *A61P 25/22* | (2006.01) |
| *C07K 16/22* | (2006.01) |
| *G01N 33/50* | (2006.01) |
| *G01N 33/68* | (2006.01) |

(52) U.S. Cl.
CPC .............. *C07K 16/22* (2013.01); *A61K 38/18* (2013.01); *A61P 25/22* (2018.01); *A61P 25/24* (2018.01); *G01N 33/50* (2013.01); *G01N 33/6893* (2013.01); *A61K 2039/505* (2013.01); *C07K 2317/21* (2013.01); *C07K 2317/76* (2013.01); *G01N 2333/475* (2013.01); *G01N 2500/04* (2013.01); *G01N 2800/30* (2013.01); *G01N 2800/301* (2013.01); *G01N 2800/304* (2013.01)

(58) Field of Classification Search
CPC .............. A61K 38/18; A61K 2039/505; G01N 33/6893; G01N 2333/475; G01N 2500/04; G01N 2800/30; G01N 2800/301; G01N 2800/304; G01N 33/50; C07K 2317/76; C07K 16/22; C07K 2317/21; A61P 25/22; A61P 25/24
See application file for complete search history.

(56) References Cited

U.S. PATENT DOCUMENTS

| | | |
|---|---|---|
| 5,408,040 A | 4/1995 | Grotendorst et al. |
| 7,405,274 B2 | 7/2008 | Lin et al. |
| 2010/0190731 A1 | 7/2010 | Olgin et al. |

FOREIGN PATENT DOCUMENTS

| | | | |
|---|---|---|---|
| WO | 00/035939 A2 | 6/2000 | |
| WO | 2005/110479 A2 | 11/2005 | |
| WO | WO-2009033743 A1 * | 3/2009 | ............. C07K 16/18 |
| WO | 2010027830 | 3/2010 | |
| WO | 2010/119295 A1 | 10/2010 | |
| WO | 2012/085555 A2 | 6/2012 | |
| WO | 2012/085557 A2 | 6/2012 | |
| WO | 2012/100262 A1 | 7/2012 | |
| WO | 2016205226 | 12/2016 | |

OTHER PUBLICATIONS

Cryan et al. Assessing substrates underlying the behavioral effects of antidepressants using the modified rat forced swimming test. Neurosci Biobehav Rev. 2005;29(4-5):547-69.*
Engin et al. The effects of intra-cerebral drug infusions on animals' unconditioned fear reactions: a systematic review. Prog Neuropsychopharmacol Biol Psychiatry. Aug. 1, 2008;32(6):1399-419. doi: 10.1016/j.pnpbp.2008.03.020. Epub Apr. 8, 2008.*
PCT/US2016/037415, International Search Report, dated Sep. 13, 2016, 3 pages.
Schwarz et al., "Identification of a Blood-based Biological Signature in Subjects with Psychiatric Disorders Prior to Clinical Manifestation," The World Journal of Biological Psychiatry, Dec. 2012, vol. 13, No. 8, pp. 627-632.
Sussulini et al., "Proteomics and Metabolomics of Bipolar Disorder," Advances in Biological Psychiatry, 2014, vol. 29, pp. 116-127.
EP Patent Application No. 16812246.3, Extended European Search Report, dated Nov. 6, 2018, 9 pages.
Turner et al., "Connective Tissue Growth Factor is a Novel Prodepressant," Biological Psychiatry, Oct. 15, 2018, vol. 84, pp. 555-562.

* cited by examiner

*Primary Examiner* — Gregory S Emch
(74) *Attorney, Agent, or Firm* — Kilpatrick Townsend & Stockton LLP

(57) ABSTRACT

The methods of the present invention are useful for determining whether an individual has or is at risk of developing an affective disorder by detecting the expression level of connective tissue growth factor (CTGF) in a biological sample. The methods of the present invention are also useful for identifying compounds that modulate (e.g., decrease) the expression level or activity of CTGF. The present invention further provides therapeutic methods that target CTGF for the treatment of an affective disorder.

8 Claims, 2 Drawing Sheets
Specification includes a Sequence Listing.

SEQUENCE LISTING

```
<160> NUMBER OF SEQ ID NOS: 6

<210> SEQ ID NO 1
<211> LENGTH: 50
<212> TYPE: DNA
<213> ORGANISM: Artificial Sequence
<220> FEATURE:
<223> OTHER INFORMATION: synthetic probe sequence

<400> SEQUENCE: 1
cagtgtcctt ggcaggctga tttctaggta ggaaatgtgg tagctcacgc           50

<210> SEQ ID NO 2
<211> LENGTH: 20
<212> TYPE: DNA
<213> ORGANISM: Artificial Sequence
```

```
<220> FEATURE:
<223> OTHER INFORMATION: synthetic forward primer sequence

<400> SEQUENCE: 2
tggagttcaa gtgccctgac                                                       20

<210> SEQ ID NO 3
<211> LENGTH: 20
<212> TYPE: DNA
<213> ORGANISM: Artificial Sequence
<220> FEATURE:
<223> OTHER INFORMATION: synthetic reverse primer sequence

<400> SEQUENCE: 3
actgctccta aagccacacc                                                       20

<210> SEQ ID NO 4
<211> LENGTH: 50
<212> TYPE: DNA
<213> ORGANISM: Artificial Sequence
<220> FEATURE:
<223> OTHER INFORMATION: synthetic probe sequence

<400> SEQUENCE: 4
ccacgaggaa gtgtttgctg cttctttgac tatgactggt ttgggaggca                      50

<210> SEQ ID NO 5
<211> LENGTH: 20
<212> TYPE: DNA
<213> ORGANISM: Artificial Sequence
<220> FEATURE:
<223> OTHER INFORMATION: synthetic forward primer sequence

<400> SEQUENCE: 5
agagtggaga tgccaggaga                                                       20

<210> SEQ ID NO 6
<211> LENGTH: 20
<212> TYPE: DNA
<213> ORGANISM: Artificial Sequence
<220> FEATURE:
<223> OTHER INFORMATION: synthetic reverse primer sequence

<400> SEQUENCE: 6
cacacaccca gctcttgcta                                                       20
```

METHOD FOR DECREASING DEPRESSION-LIKE BEHAVIOR WITH CONNECTIVE TISSUE GROWTH FACTOR (CTGF) INHIBITOR

CROSS-REFERENCE TO RELATED APPLICATION

This application is a continuation of PCT/US2016/037415, filed Jun. 14, 2016, which claims priority to U.S. Provisional Application No. 62/175,828, filed Jun. 15, 2015, the disclosures of which are hereby incorporated by reference in their entirety for all purposes.

BACKGROUND OF THE INVENTION

Psychiatric disorders include any mental disorder or illness that interferes with the way a person behaves, interacts with others, and/or functions in daily life. *The Diagnostic and Statistical Manual (DSM) of Mental Disorders*, published by the American Psychiatric Association, classifies psychiatric disorders. The latest version, the DSM-5 (Fifth Edition), lists the following categories of mental disorders: adjustment disorders; anxiety disorders; delirium, dementia, amnestic, and other cognitive disorders; disorders usually first diagnosed in infancy, childhood or adolescence, such as learning disorders or communication disorders; dissociative disorders; eating disorders; factitious disorders; impulse-control disorders; mental disorders due to a general medical condition; mood disorders; other conditions of clinical importance; personality disorders; schizophrenia and other psychotic disorders; sexual and gender identity disorders; sleep disorders; somatoform disorders; and substance-related disorders. See also, http://www.dsm5.org.

The exact cause of most psychiatric disorders is not known. Mental health experts believe that psychiatric disorders typically result from a combination of genetic or inherited dispositions and a triggering event. Triggering events may include environmental factors, stresses of various kinds, and even physical health problems. Psychiatric disorders are very common in the United States. In fact, one-fifth of the American population suffers from some sort of mental disorder during any given year, according to the American Psychiatric Association.

The current lack of biomarkers and the ineffectiveness and reliability of the diagnosis and rates are important issues for the treatment of psychiatric disorders. For example, around 15% of the population suffers from major depression, while approximately 1% suffers from bipolar disorder. However, differentiating between these two disorders is difficult and results in at least 10-15% of bipolar disorder patients being misdiagnosed as having major depression. The consequences of such misdiagnosis include a delay in being introduced to efficacious treatment with mood stabilizers and a delay in seeking or obtaining counseling specific to bipolar disorder.

Medication is widely used to treat a variety of psychiatric disorders. For example, antidepressants are used for the treatment of clinical depression as well as for anxiety and other disorders. Anxiolytics are used for anxiety disorders and related problems such as insomnia. Mood stabilizers are used primarily in bipolar disorder, mainly targeting mania rather than depression. Antipsychotics are used for psychotic disorders such as schizophrenia. Stimulants are commonly used, notably for attention deficit hyperactivity disorder (ADHD). However, there are concerns regarding the lack of efficacy, long onset of action, and side-effects associated with the use of such medications.

As such, there is a need in the art for improved methods to accurately and reliably diagnose psychiatric disorders, particularly affective disorders such as mood disorders (e.g., major depression). Moreover, despite the existence of an assortment of different medications, there is a need in the art for improved drugs to treat psychiatric disorders, particularly affective disorders such as mood disorders (e.g., major depression) and symptoms thereof. The present invention satisfies these needs and provides related advantages as well.

BRIEF SUMMARY OF THE INVENTION

The methods of the present invention are useful for determining whether an individual has or is at risk of developing an affective disorder by detecting the expression level of connective tissue growth factor (CTGF) in a biological sample. The methods of the present invention are also useful for identifying compounds that modulate (e.g., decrease) the expression level or activity of CTGF. The present invention further provides therapeutic methods that target CTGF for the treatment of an affective disorder.

In one aspect, the present invention provides a method for determining whether an individual has or is at risk of developing an affective disorder, the method comprising:
 (a) detecting the expression level of CTGF in a biological sample from the individual;
 (b) comparing the expression level of CTGF detected in the biological sample to a control expression level of CTGF; and
 (c) determining that the individual has or is at risk of developing an affective disorder when the expression level of CTGF detected in the biological sample is increased compared to a control expression level of CTGF.

In another aspect, the present invention provides a method for identifying a compound for treating an affective disorder, the method comprising:
 (a) contacting the compound with connective tissue growth factor (CTGF); and
 (b) determining whether the compound decreases the expression level or activity of CTGF, thereby identifying a compound for treating an affective disorder.

In yet another aspect, the present invention provides a method for treating an affective disorder in an individual in need thereof, the method comprising:
 (a) administering to the individual a therapeutically effective amount of a connective tissue growth factor (CTGF) inhibitor.

Other objects, features, and advantages of the present invention will be apparent to one of skill in the art from the following detailed description and figures.

DETAILED DESCRIPTION OF THE INVENTION

I. Introduction

Figure 1:
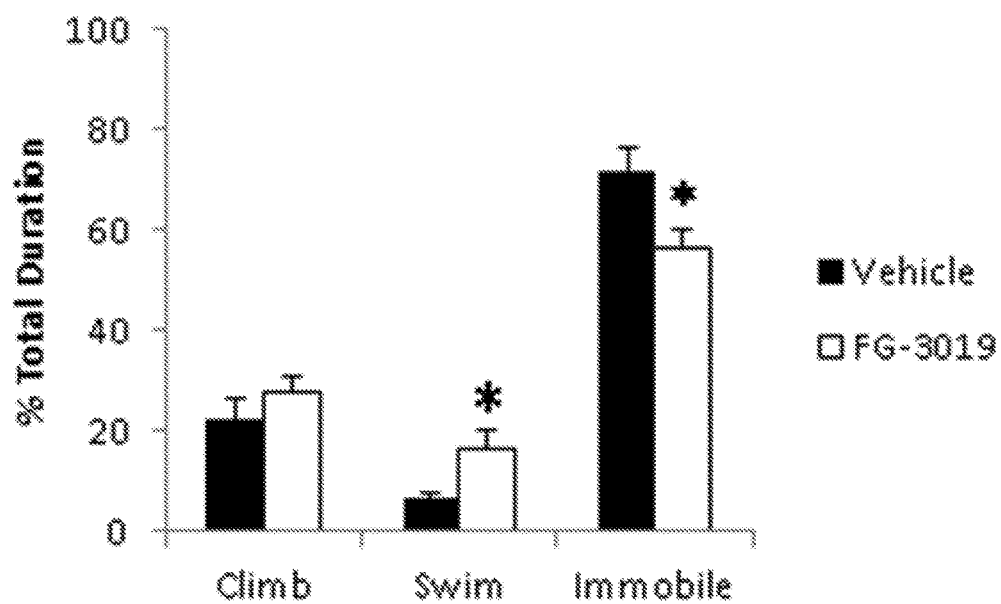
FIG. 1 illustrates that there was a significant decrease in the percent total duration that the animal was immobile and a significant increase in the percent total duration for swimming in the forced swim test (FST) after acute administration of an anti-CTGF antibody.

The present invention is based on the discovery that connective tissue growth factor (CTGF) is significantly upregulated in the amygdala of individuals with major depressive disorder (MDD) relative to controls. As such, methods of the present invention are useful for determining whether an individual has or is at risk of developing an affective disorder by detecting the expression level of CTGF in a biological sample obtained from the individual.

The present invention is also based on the discovery that administration of anti-CTGF antibodies decreased depression-like behavior in an animal model. As such, the methods of the present invention are also useful for targeting CTGF expression or activity for the treatment of an affective disorder such as MDD. In particular embodiments, the therapeutic methods described herein comprise anti-CTGF antibody therapy for producing an antidepressant effect in an individual with an affective disorder such as MDD.

II. Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "subject", "patient", or "individual" are used herein interchangeably to refer to a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

The term "connective tissue growth factor" or "CTGF" refers to a matricellular protein of the CCN family of extracellular matrix-associated heparin-binding proteins. CTGF has important roles in many biological processes, including cell adhesion, migration, proliferation, angiogenesis, skeletal development, and tissue wound repair, and is critically involved in fibrotic disease and several forms of cancers. Members of the CCN protein family, including CTGF, are structurally characterized by having four conserved, cysteine-rich domains. These domains are, from N- to C-termini, the insulin-like growth factor binding protein (IGFBP) domain, the von Willebrand type C repeats (vWC) domain, the thrombospondin type 1 repeat (TSR) domain, and a C-terminal domain with a cysteine knot motif. CTGF exerts its functions by binding to various cell surface receptors in a context-dependent manner, including integrin receptors, cell surface heparan sulfate proteoglycans (HSPGs), LRPs, and TrkA. In addition, CTGF binds growth factors and extracellular matrix proteins. The N-terminal half of CTGF interacts with aggrecan, the TSR domain interacts with VEGF, and the C-terminal domain interacts with members of the TGF-β superfamily, fibronectin, perlecan, fibulin-1, slit, and mucins. The *Homo sapiens* CTGF mRNA sequence is described, for example, in GenBank Accession No. NM_001901.2. The *Homo sapiens* CTGF polypeptide sequence is described, for example, in GenBank Accession No. NP_001892.1. CTGF is also known as CCN family member 2 (CCN2), NOV2, hypertrophic chondrocyte-specific protein 24 (HCS24), and insulin-like growth factor-binding protein 8 (IGFBP8).

The term "affective disorder" refers to any mental disorder that is characterized by abnormal disturbances of mood, feelings, or emotions. Non-limiting examples of affective disorders include mood disorders (e.g., depression of all forms and/or types, bipolar disorder, etc.), anxiety, and anxiety disorders, as described in, e.g., the Diagnostic and Statistical Manual (DSM) of Mental Disorders, Fifth Edition (DSM-5).

A "mood disorder" includes disruption of feeling, tone or emotional state experienced by an individual for an extensive period of time. Mood disorders include, but are not limited to, depression (i.e., depressive disorders), bipolar disorders, substance-induced mood disorders, alcohol-induced mood disorders, benzodiazepine-induced mood disorders, mood disorders due to general medical conditions, as well as many others. See, e.g., DSM-5.

The term "depression" or "depressive disorder" refers to a mood disorder involving any of the following symptoms: persistent sad, anxious, and/or "empty" mood; feelings of hopelessness and/or pessimism; feelings of guilt, worthlessness, and/or helplessness; loss of interest or pleasure in hobbies and activities that were once enjoyed, including sex; decreased energy, fatigue, and/or being "slowed down"; difficulty concentrating, remembering, and/or making decisions; insomnia, early-morning awakening, and/or oversleeping; loss of appetite and/or weight loss, overeating and/or weight gain; thoughts of death and/or suicide; suicide attempts; restlessness and/or irritability; persistent physical symptoms that do not respond to treatment, such as headaches, digestive disorders, and/or chronic pain; and combinations thereof. See, e.g., DSM-5. Non-limiting examples of depressive disorders include major depressive disorder (MDD), atypical depression, melancholic depression, psychotic major depression or psychotic depression, catatonic depression, postpartum depression, seasonal affective disorder (SAD), chronic depression (dysthymia), double depression, depressive disorder not otherwise specified, depressive personality disorder (DPD), recurrent brief depression (RBD), minor depressive disorder (minor depression), premenstrual syndrome, premenstrual dysphoric disorder, depression caused by chronic medical conditions (e.g., cancer, chronic pain, chemotherapy, chronic stress), and combinations thereof. Various subtypes of depression are described in, e.g., DSM-5. In particular embodiments, the depression is major depressive disorder (MDD).

"Bipolar disorder" includes a mood disorder characterized by alternating periods of extreme moods. A person with bipolar disorder experiences cycling of moods that usually swing from being overly elated or irritable (mania) to sad and hopeless (depression) and then back again, with periods of normal mood in between. Diagnosis of bipolar disorder is described in, e.g., DSM-5. Bipolar disorders include bipolar disorder I (mania with or without major depression), bipolar disorder II (hypomania with major depression), and cyclothymia. See, e.g., DSM-5. Bipolar disorder is also known as manic depression.

"Anxiety" includes a condition characterized by feelings of worry, nervousness, unease, and/or tension, typically about an imminent event or something with an uncertain outcome. Symptoms of anxiety include, without limitation, fear, panic, heart palpitations, shortness of breath, fatigue, nausea, headaches (e.g., tension headaches), tachycardia, muscle weakness and/or tension, chest pain, stomach aches, pallor, sweating, trembling, pupillary dilation, panic attacks, and combinations thereof. See, e.g., DSM-5. In certain instances, the methods of the present invention treat or alleviate one or more symptoms of anxiety. In other instances, the methods of the present invention treat anxiety or an anxiety disorder. Non-limiting examples of anxiety disorders include generalized anxiety disorder, obsessive-compulsive disorder, panic disorder, agoraphobia, posttraumatic stress disorder (PTSD), social anxiety disorder, and combinations thereof.

The term "biological sample" refers to any sample comprising biological material from any biological source that may contain an analyte (e.g., CTGF) of interest. For example, "biological sample" may include whole blood, serum, plasma, saliva, urine, cerebrospinal fluid, amniotic fluid, nipple aspirate, feces, bile, tears, perspiration, sperm, vaginal fluid, or tissue sample (e.g., brain tissue). In some embodiments, the biological sample is derived, e.g., by biopsy, from cells, tissues, or organs. In certain instances, the biological sample is a tissue sample from a specific brain region such as the amygdala (e.g., the accessory basal nucleus (AB) of the amygdala).

"Inhibitors," "activators," and "modulators" of binding, activity, or expression include inhibitory, activating, or modulating molecules, respectively, identified using in vitro and in vivo assays for binding, activity, or expression, e.g., ligands, agonists, antagonists, homologs, and mimetics thereof. The term "modulator" includes inhibitors and activators. Inhibitors are agents that, e.g., bind to a polypeptide and inhibit, partially or totally block stimulation or enzymatic activity, decrease, prevent, delay activation, inactivate, desensitize, or downregulate the activity or expression of the polypeptide; or decrease, reduce, or downregulate the expression of an mRNA that encodes the polypeptide, e.g., antagonists. Activators are agents that, e.g., bind to, stimulate, increase, open, activate, facilitate, enhance activation or enzymatic activity, sensitize or upregulate the activity or expression of a polypeptide; or increase, enhance, or upregulate the expression of an mRNA that encodes the polypeptide, e.g., agonists. Modulators include naturally-occurring and synthetic ligands, antagonists, agonists, small chemical molecules, and the like.

The term "test compound" or "drug candidate" includes any molecule, either naturally-occurring or synthetic, e.g., protein, polypeptide, peptide, small organic molecule, polysaccharide, lipid, fatty acid, polynucleotide, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. In certain embodiments, high throughput screening (HTS) methods are employed for such an analysis.

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, at least 95% pure, or at least 99% pure.

The term "nucleic acid" or "polynucleotide" includes deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "polypeptide," "peptide," and "protein" are used interchangeably herein to include a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" includes naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs include compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" include chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" include those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions and/or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and/or alleles.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. For example, recombinant cells express genes that are not found within the native (non-recombinant) form of the cell or express native genes that are otherwise abnormally expressed, under-expressed, or not expressed at all.

The term "antibody" refers to a polypeptide that is substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. Variations in amino acid sequences of the variable regions are responsible for the vast diversity of antigen-binding sites, and the greatest variability occurs throughout three hypervariable regions, termed complementary determining regions (CDRs). The tail region of the antibody, known as the $F_C$ region, is comprised of two constant domains ($C_H2$, and $C_H3$) from each of the heavy chains. The $F_C$ region is responsible for recruiting effector functions through binding of $F_C$ receptors on neutrophils and macrophages.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially a Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or those synthesized de novo using recombinant DNA methodologies (e.g., single chain Fv).

The term "humanized antibody" refers to an antibody comprising at least one chain comprising variable region framework residues substantially from a human antibody chain (referred to as the acceptor immunoglobulin or antibody) and at least one complementary determining region (CDR) substantially from a mouse antibody (referred to as the donor immunoglobulin or antibody). See, e.g., Queen et al., *Proc. Natl. Acad. Sci. USA* 86: 10029 10033 (1989), U.S. Pat. Nos. 5,530,101, 5,585,089, 5,693,761, WO 90/07861, and U.S. Pat. No. 5,225,539. The constant region(s), if present, can also be substantially or entirely from a human immunoglobulin. Methods of making humanized antibodies are known in the art. See, e.g., U.S. Pat. No. 7,256,273.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies or fragments thereof that are specifically immunoreactive with a particular protein or in a particular form. For example, solid-phase ELISA immunoassays are routinely used to select antibodies specifically immunoreactive with a protein (see, e.g., Harlow & Lane,

*Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background.

The term "interfering RNA" or "RNAi" or "interfering RNA sequence" includes single-stranded RNA (e.g., mature miRNA, ssRNAi oligonucleotides, ssDNAi oligonucleotides), double-stranded RNA (i.e., duplex RNA such as small interfering RNA (siRNA), Dicer-substrate dsRNA, shRNA, aiRNA, or pre-miRNA), a DNA-RNA hybrid, or a DNA-DNA hybrid that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. In some embodiments, the interfering RNA molecules are chemically synthesized. The interfering RNA molecules may also be generated by cleavage of longer dsRNA (e.g., dsRNA greater than about 25 nucleotides in length) with the *E. coli* RNase III or Dicer. In other embodiments, the interfering RNA molecules may be encoded by a plasmid (e.g., transcribed as sequences that automatically fold into duplexes with hairpin loops).

An individual who is "at risk of developing an affective disorder" refers to an individual (e.g., a human) who has an inclination or a higher likelihood of developing an affective disorder such as a mood disorder, anxiety, or an anxiety disorder when compared to an average individual (e.g., a human) in the general or control population.

A "therapeutically effective amount" includes an amount or quantity effective, at dosages and for periods of time necessary, to achieve the desired therapeutic or prophylactic result.

III. Detailed Description of the Embodiments

In one aspect, the present invention provides a method for determining whether an individual has or is at risk of developing an affective disorder, the method comprising:
(a) detecting the expression level of CTGF in a biological sample from the individual;
(b) comparing the expression level of CTGF detected in the biological sample to a control expression level of CTGF; and
(c) determining that the individual has or is at risk of developing an affective disorder when the expression level of CTGF detected in the biological sample is increased compared to a control expression level of CTGF.

In some embodiments, the affective disorder is a mood disorder, anxiety, or an anxiety disorder. In certain instances, the mood disorder is major depressive disorder (MDD) or bipolar disorder (BP). In preferred embodiments, the individual is a human.

In some embodiments, the expression level of CTGF is the mRNA level of CTGF. The mRNA level can be detected or measured with an assay such as, e.g., a hybridization assay or an amplification-based assay. In certain instances, microarray analysis is performed to determine or quantify CTGF mRNA levels by detecting hybridization using a probe comprising a sequence such as 5'-CAGTGTCCTTG-GCAGGCTGATTTCTAGGTAGGAAATGTGGTAGCT-CACGC-3' (SEQ ID NO:1) or a fragment thereof. In certain other instances, reverse transcription polymerase chain reaction (RT-PCR) is performed to determine or quantify CTGF mRNA levels by detecting amplification using a primer pair comprising a forward primer sequence such as 5'-TGGAGT-TCAAGTGCCCTGAC-3' (SEQ ID NO:2) or a fragment thereof and a reverse primer sequence such as 5'-ACT-GCTCCTAAAGCCACACC-3' (SEQ ID NO:3) or a fragment thereof.

In other embodiments, the expression level of CTGF is the protein level of CTGF. The protein level can be detected or measured with an assay such as, e.g., an immunoassay (e.g., ELISA), an immunohistochemical assay, or a multiplexed immunoarray.

In some embodiments, the biological sample is a whole blood, serum, plasma, saliva, urine, cerebrospinal fluid, amniotic fluid, nipple aspirate, or tissue sample. In certain instances, the tissue sample is brain tissue. The brain tissue can be from any brain region including the frontal cortex (e.g., dorsolateral prefrontal cortex), anterior cingulate cortex, cerebellar cortex, superior temporal gyrus, parietal cortex, nucleus accumbens, amygdala, or combinations thereof. In other embodiments, the method further comprises obtaining the biological sample from the individual prior to step (a).

In certain embodiments, the control expression level is the expression level (e.g., mRNA or protein level) of CTGF in an individual or a population of individuals without the affective disorder, i.e., an age and/or sex-matched control individual or a population of such control individuals. In particular embodiments, the expression level (e.g., mRNA or protein level) of CTGF detected in the biological sample is increased by more than 1-fold compared to the control expression level of CTGF. For example, the expression level (e.g., mRNA or protein level) of CTGF detected in the biological sample can be increased by more than about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, or 10-fold, or from about 1 to 2, 1 to 3, 1 to 4, 1 to 5, 1 to 6, 1 to 7, 1 to 8, 1 to 9, 1 to 10, 2 to 3, 2 to 4, or 2 to 5-fold, compared to the control expression level of CTGF. In certain instances, the expression level (e.g., mRNA or protein level) of CTGF is normalized to one or more housekeeping genes and then compared to a normalized expression level (e.g., mRNA or protein level) of CTGF in a control individual or a population of control individuals without the affective disorder in order to determine the fold difference in the expression level of CTGF. In particular embodiments, the expression level (e.g., mRNA or protein level) of CTGF detected in the amygdala or nuclei thereof (e.g., Accessory Basal (AB), AAA, AHA, Basal, and/or Lateral nucleus) of an individual (e.g., human) having or at risk of developing an affective disorder (e.g., major depressive disorder) is about 1.5, 1.6, 1.7, 1.8, 1.9, 2, or 2.1-fold higher, or from about 1 to 2, 1 to 3, 1.5 to 2.5, or 1.5 to 2-fold higher, compared to the control expression level of CTGF.

In other embodiments, the method further comprises detecting in the biological sample the expression level of a CTGF pathway member such as, e.g., ECM2, EGR1, BCL2L2, IGFBP7, P4HA1, PDGFB, MAPKAPK5, MAPK8IP3, PKN1, PRKAG1, CREB1, RHOG, RHOA, SORL1, SOX4, STK3, and/or any other member of the CTGF pathway known in the art.

In a related aspect, the present invention provides a method for diagnosing and treating an affective disorder (e.g., major depressive disorder) in an individual (e.g., human), the method comprising:
(a) detecting the expression level of connective tissue growth factor (CTGF) in a biological sample from the individual;
(b) comparing the expression level of CTGF detected in the biological sample to a control expression level of CTGF;
(c) diagnosing the individual with the affective disorder when the expression level of CTGF detected in the biological sample is increased compared to a control expression level of CTGF; and
(d) administering a therapeutically effective amount of a CTGF inhibitor to the diagnosed individual.

In another aspect, the present invention provides a method for identifying a compound for treating an affective disorder, the method comprising:
(a) contacting the compound with connective tissue growth factor (CTGF); and
(b) determining whether the compound decreases the expression level or activity of CTGF, thereby identifying a compound for treating an affective disorder.

In some embodiments, the affective disorder is a mood disorder, anxiety, or an anxiety disorder. In certain instances, the mood disorder is major depressive disorder (MDD) or bipolar disorder (BP). In preferred embodiments, the individual is a human.

In certain embodiments, the compound is contacted with a cell expressing CTGF. In particular embodiments, the compound decreases the expression level or activity of CTGF by more than 1-fold compared to the expression level or activity of CTGF not contacted with the compound. For example, the expression level or activity of CTGF contacted with the compound can be decreased by more than about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, or 10-fold, or from about 1 to 2, 1 to 3, 1 to 4, 1 to 5, 1 to 6, 1 to 7, 1 to 8, 1 to 9, 1 to 10, 2 to 3, 2 to 4, or 2 to 5-fold compared to CTGF not contacted with the compound. In certain instances, the expression level or activity of CTGF contacted with the compound is normalized to one or more housekeeping proteins and then compared to a normalized level of CTGF not contacted with the compound in order to determine the fold difference in the level or activity of CTGF.

In other embodiments, the method further comprises contacting the compound with a CTGF pathway member such as, e.g., ECM2, EGR1, BCL2L2, IGFBP7, P4HA1, PDGFB, MAPKAPK4, MAPK8IP3, PKN1, PRKAG1, CREB1, RHOG, RHOA, SORL1, SOX4, STK3, and/or any other member of the CTGF pathway known in the art. In related embodiments, the cell further expresses one or more CTGF pathway members.

In some embodiments, the method further comprises administering the compound to an animal model. In particular embodiments, the animal model is capable of identifying and evaluating individual differences in a behavior of interest, e.g., anxiety-like behavior and/or depression-like behavior. In certain instances, the animal model comprises outbred rats. In certain other instances, the animal model is selected from the group consisting of a rat model with high anxiety- and depression-like behavior ("High Responder" or bLR), a rat model with low anxiety- and depression-like behavior ("Low Responder" or bHR), and combinations thereof. See, e.g., Clinton et al., *Eur. J. Neurosci.*, 34:994-1005 (2011); Flagel et al., *Neuropharmacology*, 76:425-436(2014); Jama et al., *Psychopharmacology*, 198:333-340 (2008); and Stead et al., *Behavior Genetics*, 36:697-712 (2006). In certain embodiments, the method further comprises determining the effect of the compound on the expression level or activity of CTGF in the animal model. In other embodiments, the method further comprises determining the antidepressant and/or anxiolytic effect of the compound in the animal model.

In yet another aspect, the present invention provides a method for treating an affective disorder in an individual in need thereof, the method comprising:
(a) administering to the individual a therapeutically effective amount of a compound identified using the method described herein.

In some embodiments, the affective disorder is a mood disorder, anxiety, or an anxiety disorder. In certain instances, the mood disorder is major depressive disorder (MDD) or bipolar disorder (BP). In preferred embodiments, the individual is a human.

In other embodiments, the compound is administered intravenously, intracranially, intracerebroventricularly, intrathecally, intraspinally, intraperitoneally, intramuscularly, intralesionally, intranasally, orally, or subcutaneously.

In a further aspect, the present invention provides a method for treating an affective disorder in an individual in need thereof, the method comprising:
(a) administering to the individual a therapeutically effective amount of a connective tissue growth factor (CTGF) inhibitor.

In some embodiments, the affective disorder is a mood disorder, anxiety, or an anxiety disorder. In certain instances, the mood disorder is major depressive disorder (MDD) or bipolar disorder (BP). In preferred embodiments, the individual is a human.

In certain embodiments, the CTGF inhibitor is selected from the group consisting of an antibody or fragment thereof, an interfering RNA, a small molecule compound, and combinations thereof.

In some embodiments, the antibody is a human, humanized, or chimeric anti-CTGF monoclonal antibody or an antigen-binding fragment thereof. In particular embodiments, the anti-CTGF antibody is a neutralizing antibody. In certain embodiments, the anti-CTGF antibody is FG-3019 (CLN-1), a recombinant human IgG1 kappa monoclonal antibody, as described in U.S. Pat. No. 7,405,274 and International Patent Publication No. WO 2004/108764. In particular embodiments, the anti-CTGF antibody recognizes an epitope within domain 2 of human CTGF (e.g., FG-3019). Non-limiting examples of other anti-CTGF antibodies suitable for treating an affective disorder (e.g., by blocking the binding or activity of CTGF) include the anti-CTGF antibodies described in U.S. Pat. Nos. 5,408,040, 6,562,618, 7,541,438, 7,871,617, and 8,865,173; international Patent Publication Nos. WO 99/33878, WO 1999/007407, WO 2000/035936, WO 2007/066823, WO 2012/100262, and WO 2013/094723; and Japanese Patent Publication No. JP-A-2000-232884. Non-limiting examples of additional anti-CTGF antibodies suitable for treating an affective disorder (e.g., by blocking the binding or activity of CTGF) include the anti-CTGF neutralizing monoclonal antibodies described in Ikawa et al. (*J. Cell Physiol.*, 216: 680-7 (2008)), the anti-CTGF humanized single-chain variable fragment antibody (scFv) monomers and dimers described in Gao et al. (*PLoS ONE*, 9(12): e113980 (2014)), and the anti-CTGF neutralizing antibody available from PeproTech (Catalog Number 500-P252; London, UK).

Non-limiting examples of interfering RNA constructs suitable for treating an affective disorder (e.g., by reducing or inhibiting the expression of CTGF) include RXI-109 (a self-delivering RNAi that reduces the expression of CTGF available from RXi Pharmaceuticals), the lentiviral CTGF knockdown small hairpin RNA (shRNA) described in Lu et al. (*Ann. Hematol.,* 93:485-492 (2014)), the CTGF-specific small interfering RNA (siRNA) sequences described in Winkler et al. (*Mol Vis.,* 18:874-86 (2012); see, Table 1 of Winkler et al.), the siRNA-targeting CTGF molecules described in Luo et al. (*Transplant Proc.,* 40:2365-9 (2008)), the CTGF antisense oligonucleotide available from Biognostik GmbH, (Gottingen, Germany), the antisense oligonucleotides described in U.S. Pat. No. 7,709,630, the CTGF siRNA sequence targeting nucleotides 360-380 of the coding region relative to the first nucleotide of the start codon of the CTGF mRNA (GenBank Accession No. NM_001901) described in Croci et al. (*Cancer Res.,* 64:1730-1736 (2004)), and any interfering RNA construct designed using well-known techniques such as the methods described herein that targets the CTGF mRNA sequence (e.g., GenBank Accession No. NM_001901.2) and knocks down the expression of CTGF.

Non-limiting examples of small molecule inhibitors for treating an affective disorder (e.g., by blocking the binding or activity of CTGF or by reducing or inhibiting the expression of CTGF) include PBI-4050 (ProMetic Life Sciences Inc.), DN-9693 (Daiichi Pharmaceutical Co. Ltd.), the small molecule compounds described in U.S. Pat. No. 7,351,407 (e.g., GW-8510, purvalanol A, roscovitine, SB-216763, alsterpaullone, 9-cyanopaullone, kenpaullone, troglitazone, ciglitazone, 15(S)HETE, etc.), the HMG-CoA reductase inhibitor compounds described in U.S. Patent Publication No. 2012/0156216 (e.g., atorvastatin, berivastatin, cerivastatin, compactin, dalvastatin, dihydromevinolin, fluvastatin, glenvastatin, lovastatin, mevastatin, nisvastatin, pravastatin, pitavastatin, rivastatin, rosuvastatin, simvastatin, visastatin, etc.), and any compound identified using the screening method described herein that decreases the expression level or activity of CTGF, as well as derivatives thereof, analogs thereof, and prodrugs thereof.

In some embodiments, the CTGF inhibitor is administered intravenously, intracranially, intracerebroventricularly, intrathecally, intraspinally, intraperitoneally, intramuscularly, intralesionally, intranasally, orally, or subcutaneously. In other embodiments, the CTGF inhibitor is administered acutely or chronically to the individual. In particular embodiments, the methods of the present invention comprise acute or chronic administration of a therapeutically effective amount of an anti-CTGF antibody (e.g., FG-3019) to the individual.

In certain embodiments, a therapeutically effective amount of a CTGF inhibitor comprises a dose of about 0.5, 1, 2, 5, 10, 20, 40, 50, 75, 100, 125, 150, 175, 200, 250, 300, 400, 500, 600, 700, 750, 800, or 900 mg, or about 1, 1.5, 2, 2.5, 3, 3.5, 4, 4.5, 5, 5.5, 6, 6.5, 7, 7.5, 8, 8.5, 9, 9.5, or 10 grams (g) of the inhibitor, e.g., per day. In certain other embodiments, a therapeutically effective amount of a CTGF inhibitor comprises a dose of between about 0.001 mg/kg to about 1,000 mg/kg, about 0.01 mg/kg to about 1,000 mg/kg, about 0.1 mg/kg to about 1,000 mg/kg, about 0.1 mg/kg to about 100 mg/kg, about 1 to about 10 mg/kg, about 1 mg/kg, about 5 mg/kg, about 10 mg/kg, about 50 mg/kg, about 100 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1,000 mg/kg of the inhibitor, e.g., per day. The desired dose may be conveniently administered in a single dose, or as multiple doses administered at appropriate intervals, for example, as two, three, four, or more sub-doses per day.

In some embodiments, a therapeutically effective amount of a CTGF inhibitor is administered acutely, e.g., as a single dose or as multiple doses over a short period of time (e.g., over a span of less than about 24 hours), to an individual. In other embodiments, a therapeutically effective amount of a CTGF inhibitor is administered chronically, e.g., as repeated doses spanning hours (e.g., every 24, 48, or 72 hours), days, weeks, months, or years, to an individual. As non-limiting examples, pharmaceutical compositions comprising a CTGF inhibitor described herein can be administered at least 1, 2, 3, 4, 5, 6, 7, 8, 9, 10, or more times daily for at least 1, 2, 3, 4, 5, 6, or 7 days a week for a period of at least 1, 2, 3, 4, 5, 6, 7, 8, 9, 10, 11, 12, 13, 14, 15, 16, 17, 18, 19, 20, or more weeks or months. In certain instances, a rest period ranging from a few days (e.g., 1, 2, 3, 4, 5, 6, 7, 8, 9, 10, or more days) to a few weeks (e.g., 1, 2, 3, 4, 5, 6, 7, 8, 9, 10, or more weeks) can be introduced to improve the tolerability and/or efficacy of the treatment.

In certain embodiments, a therapeutically effective amount of a CTGF inhibitor substantially relieves one or more symptoms of depression and/or anxiety associated with the affective disorder, e.g., for about 15 minutes or more, about 30 minutes or more, about 1 hour or more, about 1 day or more, about 1 week or more, about 2 weeks or more, or about 4 weeks or more after the administration. In some embodiments, a therapeutically effective amount of a CTGF inhibitor is an amount that is sufficient to decrease depression (antidepressant effect) in the individual. In other embodiments, a therapeutically effective amount of a CTGF inhibitor is an amount that is sufficient to decrease anxiety (anxiolytic effect) in the individual.

In some embodiments, a therapeutically effective amount of a CTGF inhibitor comprises an amount that is sufficient to produce an antidepressant effect without essentially any dissociative side-effects. In other embodiments, a therapeutically effective amount of a CTGF inhibitor comprises an amount that is sufficient to produce an antidepressant effect with essentially no sedation. In yet other embodiments, a therapeutically effective amount of a CTGF inhibitor comprises an amount that does not have abuse potential (e.g., may not be habit-forming).

In some embodiments, a CTGF inhibitor described herein provides improved blood-brain barrier (BBB) penetration and is capable of readily crossing the BBB. In other embodiments, a CTGF inhibitor described herein provides improved in vivo potency and/or brain level concentration, e.g., relative to plasma levels. In yet other embodiments, a CTGF inhibitor described herein has a wide therapeutic index, provides a high therapeutic index, or combinations thereof.

IV. Detection of Gene Expression

The detection of the expression level of polynucleotides encoding connective tissue growth factor (CTGF) polypeptides in accordance with the present invention is useful for diagnostic applications, e.g., to determine whether an individual has or is at risk of developing an affective disorder. Moreover, the detection of gene expression is useful to identify modulators of the expression level of CTGF polypeptides or polynucleotides encoding the same.

In certain instances, the presence or level of CTGF is detected at the level of nucleic acid (e.g., mRNA) expression with an assay such as, for example, a hybridization assay or an amplification-based assay. In certain other instances, the presence or level of CTGF is detected at the level of protein expression using, for example, an immunoassay (e.g., ELISA), an immunohistochemical assay, or a multiplexed immunoarray.

A variety of methods of specific DNA and RNA measurement using nucleic acid hybridization techniques are known to those of skill in the art. Some methods involve an electrophoretic separation (e.g., Southern blot for detecting DNA, and Northern blot for detecting RNA), but measurement of DNA and RNA can also be carried out in the absence of electrophoretic separation (e.g., by dot blot).

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.*, 63:378-383 (1969); and John et al. *Nature*, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, "*Practice and Theory of Enzyme Immunoassays,*" Laboratory Techniques in Biochemistry and Molecular Biology, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex may later bind. Thus, the detectable labels can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden *Introduction to Immunocytochemistry*, 2nd ed., Springer Verlag, NY (1997); and in Haugland *Handbook of Fluorescent Probes and Research Chemicals*, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of RNA is measured by quantifying the amount of label fixed to the solid support by binding of the detection reagent. Typically, the presence of a modulator during incubation will increase or decrease the amount of label fixed to the solid support relative to a control incubation which does not comprise the modulator, or as compared to a baseline established for a particular reaction type. Means of detecting and quantifying labels are well known to those of skill in the art.

In preferred embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques are also appropriate. For instance, very large scale immobilized polymer arrays (VLSIPS™), available from Affymetrix, Inc. (Santa Clara, Calif.) can be used to detect changes in expression levels of a plurality of genes involved in the same regulatory pathways simultaneously. See, Tijssen, supra., Fodor et al. (1991) *Science*, 251: 767-777; Sheldon et al. (1993) *Clinical Chemistry* 39(4): 718-719, and Kozal et al. (1996) *Nature Medicine* 2(7): 753-759.

Detection can be accomplished, for example, by using a labeled detection moiety that binds specifically to duplex nucleic acids (e.g., an antibody that is specific for RNA-DNA duplexes). One preferred example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181: 153-162; Bogulayski (1986) et al. *J. Immunol. Methods* 89:123-130; Prooijen-Knegt (1982) *Exp. Cell Res.* 141:397-407; Rudkin (1976) *Nature* 265:472-473, Stollar (1970) *Proc. Nat'l Acad. Sci. USA* 65:993-1000; Ballard (1982) *Mol. Immunol.* 19:793-799; Pisetsky and Caster (1982) *Mol. Immunol.* 19:645-650; Viscidi et al. (1988) *J. Clin. Microbial.* 41:199-209; and Kiney et al. (1989) *J. Clin. Microbiol.* 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (3rd ed.) *Fundamental Immunology* Raven Press, Ltd., NY (1993); Coligan *Current Protocols in Immunology* Wiley/Greene, NY (1991); Harlow and Lane *Antibodies: A Laboratory Manual* Cold Spring Harbor Press, NY (1988); Stites et al. (eds.) *Basic and Clinical Immunology* (4th ed.) Lange Medical Publications, Los Altos, Calif., and references cited therein; Goding *Monoclonal Antibodies: Principles and Practice* (2d ed.) Academic Press, New York, N.Y., (1986); and Kohler and Milstein *Nature* 256: 495-497 (1975)). Other suitable techniques for antibody preparation include selection of libraries of recombinant antibodies in phage or similar vectors (see, Huse et al. *Science* 246:1275-1281 (1989); and Ward et al. *Nature* 341:544-546 (1989)). Specific monoclonal and polyclonal antibodies and antisera will usually bind with a $K_D$ of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild-type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system, in particular RT-PCR or real time PCR, and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation.

An alternative means for determining the level of expression of the nucleic acids of the present invention is in situ hybridization. In situ hybridization assays are well known and are generally described in Angerer et al., *Methods Enzymol.* 152:649-660 (1987). In an in situ hybridization assay, cells, preferably human cells from a brain region such as the amygdala, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

Material containing nucleic acid is routinely obtained from individuals. Such material is any biological matter from which nucleic acid can be prepared. As non-limiting examples, material can be whole blood, serum, plasma, saliva, cheek swab, sputum, or other bodily fluid or tissue that contains nucleic acid. In one embodiment, a method of the present invention is practiced with whole blood, which can be obtained readily by non-invasive means and used to prepare total RNA or genomic DNA. In another embodiment, detecting the expression level of CTGF involves amplification of an individual's nucleic acid using the polymerase chain reaction (PCR). Use of PCR for the amplification of nucleic acids is well known in the art (see, e.g., Mullis et al. (Eds.), *The Polymerase Chain Reaction*, Birkhauser, Boston, (1994)). In yet another embodiment, PCR amplification is performed using one or more fluorescently labeled primers. In a further embodiment, PCR amplification is performed using one or more labeled or unlabeled primers that contain a DNA minor groove binder.

Any of a variety of different primers can be used to amplify an individual's nucleic acid by PCR in order to detect the expression level of CTGF in a method of the invention. Such primers generally are designed to have sufficient guanine and cytosine content to attain a high melting temperature which allows for a stable annealing step in the amplification reaction. Several computer programs, such as Primer Select, are available to aid in the design of PCR primers.

Applicable PCR amplification techniques are described in, e.g., Ausubel et al., *Current Protocols in Molecular Biology*, John Wiley & Sons, Inc. New York (1999), Chapter 7 and Supplement 47; Theophilus et al., "PCR Mutation Detection Protocols," Humana Press, (2002); and Innis et al., *PCR Protocols*, San Diego, Academic Press, Inc. (1990). General nucleic acid hybridization methods are described in Anderson, "Nucleic Acid Hybridization," BIOS Scientific Publishers, 1999. Amplification or hybridization of a plurality of transcribed nucleic acid sequences (e.g., mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

A variety of methods of specific protein, polypeptide, and peptide measurement using various antibody-based techniques are known to those of skill in the art (see, Sambrook, supra). In certain instances, a variety of immunoassay techniques, including competitive and non-competitive immunoassays, can be used to detect the presence or level of CTGF in accordance with the methods described herein. The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (META); capillary electrophoresis immunoassays (CEIA); radioimmunoassays (MA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing and Nashabeh, *Electrophoresis*, 18:2184-2193 (1997); Bao, *J. Chromatogr. B. Biomed. Sci.*, 699:463-480 (1997)). Liposome immunoassays, such as flow-injection liposome immunoassays and liposome immunosensors, are also suitable for use in the present invention (see, e.g., Rongen et al., *J. Immunol. Methods,* 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., *J. Clin. Chem. Clin. Biol. Chem.,* 27:261-276 (1989)).

Antigen capture ELISA can be useful for detecting the presence or level of CTGF in accordance with the methods described herein. For example, in an antigen capture ELISA, an antibody directed to CTGF is bound to a solid phase and sample is added such that CTGF is bound by the antibody. After unbound proteins are removed by washing, the amount of bound CTGF can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and CTGF is allowed to bind to the first antibody. The amount of CTGF is quantitated by measuring the amount of a second antibody that binds CTGF. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) labeled secondary antibody (Harlow and Lane, supra) is also suitable for use in the present invention. A secondary antibody labeled with a chemiluminescent marker can also be suitable for use in the present invention. A chemiluminescence assay using a chemiluminescent secondary antibody is suitable for sensitive, non-radioactive detection of expression levels. Such secondary antibodies can be obtained commercially from various sources, e.g., Amersham Lifesciences, Inc. (Arlington Heights, Ill.).

Specific immunological binding of an antibody to CTGF can be detected directly or indirectly. Direct labels include fluorescent or luminescent tags, metals, dyes, radionuclides, and the like, attached to the antibody. An antibody labeled with iodine-125 ($^{125}$I) can be used for determining CTGF levels in a sample. A chemiluminescence assay using a chemiluminescent antibody specific for CTGF is suitable for sensitive, non-radioactive detection of CTGF levels. An antibody labeled with fluorochrome is also suitable for determining CTGF levels in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-α-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of CTGF levels can be made using a spectrophotometer such as an EMAX Microplate Reader (Molecular Devices; Menlo Park, Calif.) in accordance with the manufacturer's instructions. If desired, the assays described herein can be automated or performed robotically, and the signal from multiple samples can be detected simultaneously.

Flow cytometry can be used to detect the presence or level of CTGF. Such flow cytometric assays include bead-based immunoassays (see, e.g., Bishop and Davis, *J. Immunol. Methods*, 210:79-87 (1997); McHugh et al., *J. Immunol. Methods*, 116:213 (1989); Scillian et al., *Blood*, 73:2041 (1989)).

Phage display technology for expressing a recombinant antigen specific for CTGF can also be used. Phage particles expressing an antigen specific for CTGF can be anchored, if desired, to a multi-well plate using an antibody such as an anti-phage monoclonal antibody (Felici et al., "Phage-Displayed Peptides as Tools for Characterization of Human Sera" in Abelson (Ed.), *Methods in Enzymol.*, 267, San Diego: Academic Press, Inc. (1996)).

Quantitative Western blotting can also be used to detect or determine the presence or level of CTGF in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.*, 28:669-675 (1998).

Alternatively, a variety of immunohistochemical assay techniques can be used to detect or determine the presence or level of CTGF in a sample. The term "immunohistochemical assay" encompasses techniques that utilize the visual detection of fluorescent dyes or enzymes coupled (i.e., conjugated) to antibodies that react with CTGF using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays.

Alternatively, the presence or level of CTGF can be determined by detecting or quantifying the amount of purified CTGF. Purification of CTGF can be achieved, for example, by high pressure liquid chromatography (HPLC), alone or in combination with mass spectrometry (e.g., MALDI/MS, MALDI-TOF/MS, SELDI-TOF/MS, tandem MS, etc.). Qualitative or quantitative detection of CTGF can also be determined by well-known methods including, without limitation, Bradford assays, Coomassie blue staining, silver staining, assays for radiolabeled protein, and mass spectrometry.

The analysis of CTGF and one or more CTGF pathway members may be carried out separately or simultaneously with one test sample. For separate or sequential assay of CTGF and one or more CTGF pathway members, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of CTGF and one or more CTGF pathway members on a single surface. Particularly useful physical formats comprise surfaces having a plurality of discrete, addressable locations for the detection of CTGF and one or more CTGF pathway members. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize CTGF and one or more CTGF pathway members for detection at each location. Surfaces may alternatively comprise one or more discrete particles (e.g., microparticles or nanoparticles) immobilized at discrete locations of a surface, where the microparticles comprise antibodies to immobilize CTGF and one or more CTGF pathway members for detection.

V. Selection of Therapeutic Antibodies

In certain aspects, the present invention provides a method for treating an affective disorder in an individual by administering an antibody or fragment thereof that acts as a connective tissue growth factor (CTGF) inhibitor. In particular embodiments, the CTGF inhibitor is an antibody or fragment thereof that neutralizes the CTGF protein by binding to and inhibiting, partially or totally blocking stimulation or activity, decreasing, preventing, or delaying activation, or inactivating, desensitizing, or downregulating the activity or expression of the CTGF protein.

The term "antibody" includes whole antibodies and any antigen-binding fragment or a single chain thereof. Thus, an antibody includes any protein or peptide-containing molecule that comprises at least a portion of an immunoglobulin molecule, such as, but not limited to, at least one complementarity determining region (CDR) of a heavy or light chain or a ligand binding portion thereof, a heavy chain or light chain variable region, a heavy chain or light chain constant region, a framework (FR) region, or any portion thereof. Antibodies include intact immunoglobulin molecules as well as to fragments thereof, such as Fab, F(ab')2, and Fv fragments, as well as recombinant, synthetic, and genetically engineered versions thereof, which are capable of binding the epitopic determinant, and include polyclonal and monoclonal antibodies.

Anti-CTGF antibodies (e.g., antibodies that bind CTGF or fragments of CTGF) can be prepared using intact CTGF polypeptides or using fragments containing small peptides of interest as the immunizing antigen. The polypeptide or oligopeptide used to immunize an animal (e.g., a mouse, rat, rabbit, chicken, turkey, goat, etc.) can be derived, for example, from proteolysis of the CTGF protein, the translation of CTGF mRNA, or synthesized chemically, and can be conjugated to a carrier protein if desired. Commonly used carriers chemically coupled to peptides include, for example, bovine serum albumin (BSA), thyroglobulin, and keyhole limpet hemocyanin (KLH). Other methods of selecting antibodies (e.g., phage display) having desired specificities are well known in the art.

The term "antibody" is further intended to encompass antibodies, protease digestion fragments thereof, specified portions and variants thereof, including antibody mimetics or comprising portions of antibodies that mimic the structure and/or function of an antibody or specified fragment or portion thereof, including single chain antibodies and antigen-binding fragments thereof. Examples of antigen-binding fragments of an antibody include, but are not limited to: (i) a Fab fragment, a monovalent fragment consisting of the VL, VH, CL, and CH domains; (ii) a F(ab')2 fragment, a bivalent fragment comprising two Fab fragments linked by a disulfide bridge at the hinge region; (iii) a Fd fragment consisting of the VH and CH domains; (iv) a Fv fragment consisting of the VL and VH domains of a single arm of an antibody; (v) a dAb fragment (see, e.g., Ward et al., *Nature*, 341:544-546 (1989)), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al., *Science*, 242:423-426 (1988); and Huston et al., *Proc. Natl. Acad Sci. USA*, 85:5879-5883 (1988)). These antibody fragments are obtained using conventional techniques known to those of skill in the art, and the fragments are screened for utility in the same manner as are intact antibodies.

The term "neutralizing antibody" as used herein refers to an antibody, preferably a monoclonal antibody, that is capable of substantially inhibiting or eliminating a biological activity of CTGF. Typically, a neutralizing antibody will inhibit binding of CTGF to a cofactor such as TGF, to a CTGF-specific receptor associated with a target cell, or to another biological target.

The term "anti-CTGF antibody" refers to an antibody that specifically binds to CTGF (e.g., recognizes an epitope of a CTGF protein or fragment thereof). As used herein, "specific binding" refers to antibody binding to a predetermined antigen with high affinity. Typically, the antibody binds the antigen with a dissociation constant (Ku) of about $10^{-7}$ M or less, and binds to the predetermined antigen with a Ku that is at least about 1.5-fold less (e.g., at least about 2-fold less, at least about 5-fold less, etc.) than its Ku for binding to a non-specific antigen (e.g., BSA; casein) other than the predetermined antigen or a closely-related antigen. A high-affinity antibody typically has an affinity at least on the order of about $10^{-8}$ M, $10^{-9}$ M, or $10^{-10}$ M. In particular embodiments, an antibody for use in the present methods will have a binding affinity for CTGF between about $10^{-8}$ M and $10^{-10}$ M, between about $10^{-8}$ M and $10^{-9}$ M, or between about $10^{-9}$ M and $10^{-10}$ M. In particular embodiments, anti-CTGF antibodies used in the methods of the present invention have a $K_D$ for CTGF of about $10^{-8}$ M or less.

The term "naked antibody" as used herein is an antibody that is not conjugated to a cytotoxic moiety or radiolabel. In some embodiments, the anti-CTGF antibody is a naked antibody.

In some embodiments, the anti-CTGF antibody is FG-3019 (CLN-1) or mAb1 as described in International Patent Publication No. WO 2004/108764 and U.S. Pat. Nos. 7,405,274 and 8,865,173, an antibody that binds to the same epitope, or an antibody substantially equivalent thereto or derived therefrom. In particular embodiments, the anti-CTGF antibody is FG-3019 (CLN-1). In other embodiments, the anti-CTGF antibody is human monoclonal antibody M84 or M32.0 as described in Japanese Patent Publication No. JP-A-2000-232884, or mouse monoclonal antibody CTGF-m2-1 as described in International Patent Publication No. WO 2007/066823. Additional exemplary antibodies for use in the methods of the present invention are described, e.g., in U.S. Pat. Nos. 5,408,040, 6,562,618, 7,541,438, and 7,871,617; and International Patent Publication Nos. WO 99/33878, WO 1999/007407, WO 2000/035936, WO 2012/100262, and WO 2013/094723. In some embodiments, the anti-CTGF antibody has the amino acid sequence of the antibody produced by the cell line identified by ATCC Accession No, PTA-6006. In other embodiments, the anti-CTGF antibody binds to CTGF competitively with an antibody produced by the cell line identified by ATCC Accession No. PTA-6006. In further embodiments, the anti-CTGF antibody binds to the same epitope as the antibody produced by ATCC Accession No. PTA-6006.

In certain embodiments, the anti-CTGF antibody is an antibody mimetic. Antibody mimetics are proteins, typically in the range of 3-25 kDa, that are designed to bind an antigen with high specificity and affinity like an antibody, but are structurally unrelated to antibodies. Typically, antibody mimetics are based on a structural motif or scaffold that can be found as a single or repeated domain from a larger biomolecule.

VI. Selection of Interfering RNA Molecules

In certain aspects, the present invention provides a method for treating an affective disorder in an individual by administering an interfering RNA molecule that reduces or inhibits the expression of connective tissue growth factor (CTGF). Non-limiting examples of interfering RNA include single-stranded RNA (e.g., mature miRNA, ssRNAi oligonucleotides, ssDNAi oligonucleotides), double-stranded RNA (i.e., duplex RNA such as small interfering RNA (siRNA), Dicer-substrate dsRNA, small hairpin RNA (shRNA), aiRNA, or pre-miRNA), a DNA-RNA hybrid, or a DNA-DNA hybrid that is capable of reducing or inhibiting the expression of CTGF (e.g., by mediating the degradation or inhibiting the translation of CTGF mRNA). In particular embodiments, the interfering RNA is an siRNA or shRNA.

Suitable siRNA sequences can be identified using any means known in the art. Typically, the methods described in Elbashir et al., *Nature*, 411:494-498 (2001) and Elbashir et al., *EMBO J.*, 20:6877-6888 (2001) are combined with rational design rules set forth in Reynolds et al., *Nature Biotech.*, 22(3):326-330 (2004).

As a non-limiting example, the nucleotide sequence 3' of the AUG start codon of a transcript from the target gene of interest may be scanned for dinucleotide sequences (e.g., AA, NA, CC, GG, or UU, wherein N=C, G, or U) (see, e.g., Elbashir et al., *EMBO J.*, 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (i.e., an antisense strand sequence) can be designed. A potential siRNA sequence can also be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://ihome.ust.hk/~bokcmho/siRNA/siRNA.html. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal foldback structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., *Cell*, 115:209-216 (2003); and Schwarz et al., *Cell*, 115:199-208 (2003). In other embodiments, potential siRNA sequences may be further analyzed based on secondary structure at the target site as described in, e.g., Luo et al., *Biophys. Res. Commun.*, 318:303-310 (2004). For example, secondary structure at the target site can be modeled using the Mfold algorithm (available at http://mfold.burnet.edu.au/rna_form) to select siRNA sequences which favor accessibility at the target site where less secondary structure in the form of base-pairing and stem-loops is present.

A "small hairpin RNA" or "short hairpin RNA" or "shRNA" includes a short RNA sequence that makes a tight hairpin turn that can be used to silence gene expression via RNA interference. The shRNA may be chemically synthesized or transcribed from a transcriptional cassette in a DNA plasmid. The shRNA hairpin structure is cleaved by the cellular machinery into siRNA, which is then bound to the RNA-induced silencing complex (RISC).

Non-limiting examples of shRNA include a double-stranded polynucleotide molecule assembled from a single-stranded molecule, where the sense and antisense regions are linked by a nucleic acid-based or non-nucleic acid-based linker or loop structure; and a double-stranded polynucleotide molecule with a hairpin secondary structure having self-complementary sense and antisense regions. Additional shRNA sequences include, but are not limited to, asymmetric shRNA precursor polynucleotides such as those described in PCT Publication Nos. WO 2006/074108 and WO 2009/076321.

A "Dicer-substrate dsRNA" or "precursor RNAi molecule" includes any precursor molecule that is processed in vivo by Dicer to produce an active siRNA which is incorporated into the RISC complex for RNA interference of a target gene. Methods for designing and synthesizing Dicer-substrate dsRNAs are described, e.g., in U.S. Patent Publication Nos. 20050244858, 20050277610, and 20070265220.

Like siRNA, asymmetrical interfering RNA (aiRNA) can recruit the RNA-induced silencing complex (RISC) and lead to effective silencing of a variety of genes in mammalian cells by mediating sequence-specific cleavage of the target sequence between nucleotide 10 and 11 relative to the 5' end of the antisense strand (Sun et al., *Nat. Biotech.*, 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, aiRNA molecules may be designed, synthesized, and annealed under conditions similar to those used for siRNA molecules. As a non-limiting example, aiRNA sequences may be selected and generated using the methods described above for selecting siRNA sequences.

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to down-regulate gene expression. The identification of miRNA molecules is described, e.g., in Lagos-Quintana et al., *Science,* 294:853-858; Lau et al., *Science,* 294:858-862; and Lee et al., *Science,* 294:862-864.

The genes encoding miRNA are much longer than the processed mature miRNA molecule. miRNA are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., *Nature,* 432:231-235 (2004)). These pre-miRNA are then processed to mature miRNA in the cytoplasm by interaction with the endonuclease Dicer, which also initiates the formation of the RNA-induced silencing complex (RISC) (Bernstein et al., *Nature,* 409: 363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., *Curr. Biol.*, 16:530-535 (2006)). The remaining strand, known as the anti-guide or passenger strand, is degraded as a RISC complex substrate (Gregory et al., *Cell*, 123:631-640 (2005)). After integration into the active RISC complex, miRNAs base pair with their complementary mRNA molecules and induce target mRNA degradation and/or translational silencing.

Mammalian miRNA molecules are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNA may also target methylation of genomic sites which correspond to targeted mRNA. Generally, miRNA function in association with a complement of proteins collectively termed the miRNP.

The term "antisense oligonucleotide" or "antisense" includes oligonucleotides that are complementary to a targeted polynucleotide sequence. Antisense oligonucleotides are single strands of DNA or RNA that are complementary to a chosen sequence. Antisense RNA oligonucleotides prevent the translation of complementary RNA strands by binding to the RNA. Antisense DNA oligonucleotides can be used to target a specific, complementary (coding or non-coding) RNA. If binding occurs, this DNA/RNA hybrid can be degraded by the enzyme RNase H. In a particular embodiment, antisense oligonucleotides comprise from about 10 to about 60 nucleotides, more preferably from about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, $T_m$, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., *Nucleic Acids Res.*, 25:3389-402 (1997)).

VII. Screening for Modulators of CTGF Expression

A number of different screening protocols can be utilized to identify compounds that modulate the level of expression or activity of connective tissue growth factor (CTGF) in cells, particularly mammalian cells, and especially human cells. In general terms, the screening methods involve screening a plurality of compounds to identify a compound that modulates (e.g., neutralizes) the expression level or activity of CTGF by binding to CTGF, by inhibiting the expression of CTGF, by inhibiting the binding of another molecule to CTGF, and the like.

A. Binding Assays

Preliminary screens can be conducted by screening for compounds capable of binding to CTGF, as at least some of the compounds so identified are likely modulators of CTGF expression and/or activity. The binding assays usually involve contacting CTGF with one or more test compounds and allowing sufficient time for CTGF and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots. The CTGF utilized in such assays can be naturally expressed, cloned, or synthesized. Binding assays are also useful, e.g., for identifying antibodies, receptors, or other molecules that bind CTGF.

B. Expression Assays

Certain screening methods involve screening for a compound that up or down-regulates the expression (e.g., mRNA or protein level) of CTGF. Such methods generally involve conducting cell-based assays in which test compounds are contacted with one or more cells expressing CTGF and then detecting an increase or decrease in expression (either transcript, translation product, or catalytic product). Some assays are performed with peripheral cells, or other cells, that express endogenous CTGF.

Polypeptide or polynucleotide expression can be detected in a number of different ways. As a non-limiting example, the expression level of a polynucleotide can be determined by probing the mRNA expressed in a cell with a probe that specifically hybridizes with a transcript (or complementary nucleic acid derived therefrom) of CTGF. Probing can be conducted by lysing the cells and conducting Northern blots or without lysing the cells using in situ hybridization techniques. Alternatively, the expression level of a polypeptide can be detected using immunological methods in which a cell lysate is probed with antibodies that specifically bind to CTGF.

Other cell-based assays are reporter assays conducted with cells that do not express CTGF. Certain of these assays are conducted with a heterologous nucleic acid construct that includes a promoter of a polynucleotide encoding CTGF that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, chloramphenicol acetyl transferase (CAT); Alton and Vapnek (1979) *Nature* 282:864-869), luciferase, β-galactosidase, green fluorescent protein (GFP) and alkaline phosphatase (Toh et al. (1980) *Eur. J. Biochem.* 182:231-238; and Hall et al. (1983) *J. Mol. Appl. Gen.* 2:101).

In these assays, cells harboring the reporter construct are contacted with a test compound. A test compound that either activates the promoter by binding to it or triggers a cascade that produces a molecule that activates the promoter causes expression of the detectable reporter. Certain other reporter assays are conducted with cells that harbor a heterologous construct that includes a transcriptional control element that activates expression of a polynucleotide encoding CTGF and a reporter operably linked thereto. Here, too, a compound that binds to the transcriptional control element to activate expression of the reporter or that triggers the formation of a compound that binds to the transcriptional control element to activate reporter expression, can be identified by the generation of signal associated with reporter expression.

The level of expression or activity of CTGF can be compared to a baseline value. As indicated above, the baseline value can be a value for a control sample or a statistical value that is representative of expression levels for a control population (e.g., healthy individuals not having or at risk for affective disorders). Expression levels can also be determined for cells that do not express CTGF as a negative control. Such cells generally are otherwise substantially genetically the same as the test cells.

A variety of different types of cells can be utilized in the reporter assays. Cells that express endogenous CTGF include, e.g., brain cells, including cells from the frontal cortex (e.g., dorsolateral prefrontal cortex), cerebellum, anterior cingulate cortex, amygdala, hippocampus, or nucleus accumbens. Cells that do not endogenously express CTGF can be prokaryotic, but are preferably eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the COS, CHO and HeLa cell lines.

Various controls can be conducted to ensure that an observed activity is authentic including running parallel reactions with cells that lack the reporter construct or by not contacting a cell harboring the reporter construct with test compound. Compounds can also be further validated as described below.

C. Validation

Compounds that are initially identified by any of the foregoing screening methods can be further tested to validate the apparent activity. Preferably, such studies are conducted with suitable animal models. The basic format of such methods involves administering a lead compound identified during an initial screen to an animal that serves as a model for humans and then determining if the expression or activity of CTGF is in fact modulated (e.g., increased or decreased). The animal models utilized in validation studies generally are mammals of any kind. Specific examples of suitable animals include, but are not limited to, primates (e.g., monkeys), mice, and rats.

In particular embodiments, the animal model is selected from the group consisting of outbred rats, a rat model with high anxiety- and depression-like behavior (bLR), a rat model with low anxiety- and depression-like behavior (bHR), and combinations thereof. In certain embodiments, the effect of a compound on the expression level or activity of CTGF is determined in an animal model. In other embodiments, the antidepressant and/or anxiolytic effect of the compound is determined in an animal model.

D. Exemplary Modulators

The compounds tested as modulators of CTGF can be any small chemical compound or a biological entity such as a protein, polypeptide, peptide, antibody or antigen-binding fragment thereof, sugar, polysaccharide, oligosaccharide, polynucleotide, oligonucleotide, or lipid. Typically, test compounds will be small chemical molecules, proteins or polypeptides, or antibodies or antigen-binding fragments thereof. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like. Modulators also include agents designed to reduce the level of CTGF mRNA (e.g. siRNA molecules, shRNA molecules, antisense molecules, ribozymes, DNAzymes, and the like) or the level of translation from an mRNA.

In certain embodiments, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to, peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), and small organic molecule libraries.

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md., etc.).

E. Solid State and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds are possible using the integrated systems of the invention. More recently, microfluidic approaches to reagent manipulation have been developed.

The molecule of interest can be bound to the solid state component directly or indirectly via covalent or non-covalent linkage, e.g., via a tag. The tag can be any of a variety of components. In general, a molecule that binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (e.g., avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, immunoglobulin receptors, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids, and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids. Such flexible linkers are known to those of skill in the art. For example, poly(ethylene glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank and Doring, *Tetrahedron* 44:60316040 (1988) (describing synthesis of various peptide sequences on cellulose disks); Fodor et al., *Science*, 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

In certain aspects, the present invention provides in vitro assays for identifying, in a high throughput format, compounds that can modulate the expression or activity of CTGF. In some embodiments, the methods of the present invention include a control reaction. For each of the assay formats described, "no modulator" control reactions that do not include a modulator provide a background level of binding activity.

In some assays, it will be desirable to have positive controls to ensure that the components of the assays are working properly. At least two types of positive controls are appropriate. First, a known activator of CTGF can be incubated with one sample of the assay, and the resulting increase in signal resulting from an increased expression level or activity of CTGF determined according to the methods described herein. Second, a known inhibitor of CTGF can be added, and the resulting decrease in signal for the expression or activity can be similarly detected.

F. Computer-Based Assays

Yet another assay for compounds that modulate the expression or activity of CTGF involves computer assisted drug design, in which a computer system is used to generate a three-dimensional structure of CTGF based on the structural information encoded by its amino acid or nucleotide sequence. The input sequence interacts directly and actively with a pre-established algorithm in a computer program to yield secondary, tertiary, and quaternary structural models of the molecule. Similar analyses can be performed on potential ligands or binding partners of CTGF. The models of the protein or nucleotide structure are then examined to identify regions of the structure that have the ability to bind CTGF. These regions are then used to identify polypeptides that bind to CTGF.

The three-dimensional structural model of a protein is generated by entering protein amino acid sequences of at least 10 amino acid residues or corresponding nucleic acid sequences encoding CTGF into the computer system. The amino acid sequences encoded by the nucleic acid sequences represent the primary sequences or subsequences of the proteins, which encode the structural information of the proteins. At least 10 residues of an amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary, and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of CTGF to identify binding sites of CTGF. Binding affinity between CTGF and ligands is determined using energy terms to determine which ligands have an enhanced probability of binding to CTGF.

VIII. Administration and Pharmaceutical Compositions

In certain aspects, the therapeutic agents (e.g., CTGF inhibitors) described herein are administered directly to an individual (e.g., a human). Administration is by any of the routes normally used for introducing an agent into contact with a tissue to be treated and is well known to those of skill in the art. Although more than one route can be used to administer a particular composition, a particular route can often provide a more immediate and more effective reaction than another route.

In some embodiments, the therapeutic agents described herein can be combined with other drugs useful for treating affective disorders or symptoms thereof. In some embodiments, the pharmaceutical compositions of the present invention may comprise one or more CTGF inhibitors combined with at least one additional compound useful for treating affective disorders or symptoms thereof.

The pharmaceutical compositions of the invention may comprise a pharmaceutically acceptable carrier. In certain aspects, pharmaceutically acceptable carriers are determined in part by the particular composition being administered, as well as by the particular method used to administer the composition. Accordingly, there is a wide variety of suitable formulations of pharmaceutical compositions of the present invention (see, e.g., *REMINGTON'S PHARMACEUTICAL SCIENCES*, 18TH ED., Mack Publishing Co., Easton, Pa. (1990)).

The pharmaceutical compositions of the invention are administered in a manner compatible with the dosage formulation, and in such amount as will be therapeutically effective. The quantity to be administered depends on a variety of factors including, e.g., the age, body weight, physical activity, and diet of the individual, the affective disorder to be treated, and the stage or severity of the affective disorder. In certain embodiments, the size of the dose may also be determined by the existence, nature, and extent of any adverse side effects that accompany the administration of a particular therapeutic agent in a particular individual. In general, the dose equivalent of a therapeutic agent is from about 1 ng/kg to about 10 mg/kg for a typical individual.

In certain embodiments, the dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

In the practice of this invention, the compositions can be administered, for example, intravenously, intracranially, intrathecally, intraspinally, intraperitoneally, intramuscularly, intralesionally, intranasally, subcutaneously, intracerebroventricularly, orally, topically, and/or by inhalation.

As used herein, the term "unit dosage form" refers to physically discrete units suitable as unitary dosages for humans and other mammals, each unit containing a predetermined quantity of a therapeutic agent calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the therapeutic agent.

Methods for preparing such dosage forms are known to those skilled in the art (see, e.g., *REMINGTON'S PHARMACEUTICAL SCIENCES*, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *REMINGTON'S PHARMACEUTICAL SCIENCES*, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with a therapeutic agent described herein, any of the following: a diluent such as lactose, sucrose, dicalcium phosphate, and the like; a disintegrant such as starch or derivatives thereof a lubricant such as magnesium stearate and the like; and a binder such a starch, gum acacia, polyvinylpyrrolidone, gelatin, cellulose and derivatives thereof. A therapeutic agent can also be formulated into a suppository disposed, for example, in a polyethylene glycol (PEG) carrier.

Liquid dosage forms can be prepared by dissolving or dispersing a therapeutic agent and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. A therapeutic agent can also be formulated into a retention enema.

For topical administration, the therapeutically effective dose can be in the form of emulsions, lotions, gels, foams, creams, jellies, solutions, suspensions, ointments, and transdermal patches. For administration by inhalation, a therapeutic agent can be delivered as a dry powder or in liquid form via a nebulizer. Aerosol formulations can be placed into pressurized acceptable propellants such as dichlorodifluoromethane. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

IX. Examples

The following examples are offered to illustrate, but not to limit, the claimed invention.

Example 1. Acute and Chronic Administration of an Anti-CTGF Antibody Decreased Depression-Like Behavior This example illustrates that both acute and chronic administration of an anti-CTGF antibody decreased depression-like behavior in an animal model, demonstrating the utility of anti-CTGF antibody therapy for providing an antidepressant effect.

Experimental Procedures

In vivo test system: A recombinant human IgG1 kappa monoclonal antibody (FG-3019) was administered and depression-like behavior as well as anxiety-like behavior were tested in outbred rats. Acute and chronic studies were performed for both depression-like and anxiety-like behavior.

Forced Swim Test (FST)

The FST was performed between 0800 and 1130 to evaluate depression-like behavior. Rats were placed in cylinders filled with water at 25° C. so that their tails did not touch the bottom. On day one the trial consisted of 15 minutes, and on day two the trial consisted of 5 minutes. The animals were injected immediately after day one. The test was recorded by a video camera and swimming, climbing and immobility were scored by an observer blind to the experimental group using Observer software (Noldus Information Technology). Swimming and climbing were defined as the horizontal and vertical movements of the animals, respectively. Immobility was defined as the minimal amount of movement necessary to keep the animal afloat.

Elevated Plus-Maze (EPM)

The elevated plus maze was constructed of black Plexiglas, with four elevated arms (70 cm from the floor, 45 cm long, and 12 cm wide). The arms were arranged in a cross, with two opposite arms enclosed by 45-cm-high walls, and the other two arms open. At the intersection of the open and closed arms, there was a central 12×12 cm square platform giving access to all arms. The test room was dimly lit (approximately 40 lux), and behavior was monitored by a computerized video tracking system (Noldus Ethovision, Leesburg, Va.). At the beginning of the 5 minutes test, each rat was placed in the central square facing a closed arm. The computerized tracking system recorded the latency to first enter the open arm, the amount of time spent in the open arm, closed arm, and center square over the course of the 5 minute test. Testing was performed between 0800 and 1130.

Additional Methods

Methods for termination of the animals: Decapitation.

Post-mortem analysis: Microarray analysis and mRNA in situ hybridization of serial brain sections from the hippocampus and qRT-PCR of dissected hippocampi were performed.

Experimental end points of in vivo test: FST: Percent Total Duration of Climbing, Swimming and Immobility; EPM: Time Spent in the Open Arms, Closed Arms and Center Square, as well as the number of entries into each quadrant; LDB: Time Spent in the Light and Dark Quadrants, as well as the latency to enter the light.

Experimental end points of post-mortem analysis: Normalized Gene Expression, Integrated Optical Density and Fold-Change.

Methods for data analysis: Values for each subject in each group were analyzed between groups in SPSS using the appropriate statistical analysis.

Methods for statistical evaluation: Student's t-test; One-way ANOVA; Two-way ANOVA with posthoc comparisons.

Results

Acute Study of FG-3019 on Emotionality

Five days after cannula implantation into the left lateral ventricle, the animals were injected with FG-3019 or control huIgG intracerebroventricularly (i.c.v.) at a dose of 20 µg in a volume of 1 µl at a flow rate of 1 µl/min. Five to ten minutes later the animals were tested on the elevated plus-maze (EPM) for five minutes and the frequency and duration in the center, open arms and closed arms were quantified. Five days later the animals were given a 15 minute swim. One hour after swimming, the animals were injected with either FG-3019 or huIgG. The animals were then tested on the forced swim test (FST) for climbing, swimming and immobility 24 hours after the injection (day 2) for five minutes. On the EPM, there were no significant differences in time spent in the center, open arms, or closed arms. On the FST, there was a significant decrease in the percent total duration that the animal was immobile and a significant increase in the percent total duration for swimming (FIG. 1). These results demonstrate that this dose of FG-3019 decreases depression-like behavior, indicating that it acts as an antidepressant.

Chronic Study of FG-3019 on Emotionality

Figure 2:
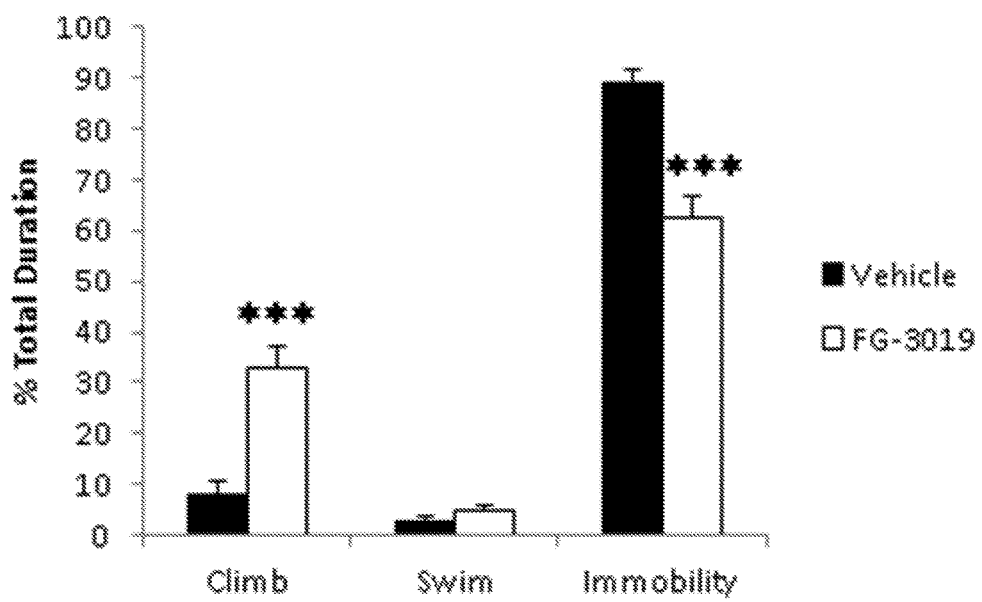
FIG. 2 illustrates that there was a significant decrease in the percent total duration for immobility and a significant increase in the percent total during for climbing in the forced swim test (FST) after chronic administration of an anti-CTGF antibody.

Five days after cannula implantation into the left lateral ventricle, the animals were injected with FG-3019 or control huIgG intracerebroventricularly (i.c.v.) at a dose of 20 µg in a volume of 1 µl at a flow rate of 1 µl/min. The rats were injected every 48 hours for a total of 7 injections over 14 days. The rats were tested for locomotor activity on day 11, on the EPM on day 12, and in the FST on days 13 and 14. There was a significant decrease in the percent total duration for immobility (FIG. 2). This result agrees with the acute study and demonstrates that FG-3019 decreases depression-like behavior, indicating that it acts as an antidepressant. Chronic treatment with FG-3019 (i.c.v.) also significantly decreased CTGF expression in the dentate gyrus of the hippocampus by 14.6%.

Example 2. Increased CTGF Expression in Post-Mortem Human Amygdala Nuclei

This example illustrates that CTGF is significantly upregulated in the amygdala of individuals with major depressive disorder (MDD) relative to controls. CTGF gene expression was initially assessed in different amygdala nuclei by Illumina Human Expression BeadChips and analyzed by BeadStudio. The probe sequence used for the microarray analysis was: 5'-CAGTGTCCTTGGCAGGCT-GATTTCTAGGTAGGAAATGTGGTAGCTCACGC-3' (SEQ ID NO:1). Following the microarray experiments, RT-PCR was performed using fresh RNA extracted from different amygdala nuclei. Equal amounts of high quality RNA were loaded into the cDNA synthesis. The cDNA was then diluted 1:10 and used in PCR reactions. The PCR primers were previously validated using standard curves and melt-curves. The primer sequences were as follows: forward, 5'-TGGAGTTCAAGTGCCCTGAC-3' (SEQ ID NO:2); and reverse, 5'-ACTGCTCCTAAAGCCACACC-3' (SEQ ID NO:3).

The relationship between CTGF and MDD was quite strong in the Accessory Basal Nucleus (AB) of the amygdala, with one probe showing a p-value of 2.44E-11 and the other probe a p-value of 1.61 E-08. See, Table 1. Several other amygdala nuclei had similar significant upregulation of CTGF in MDD (AAA, AHA, Basal, Lateral). See, Table 1. Notably, in the amygdala, MDD individuals had significantly higher CTGF expression (i.e., 1.59-fold to 2.06-fold) than controls depending on the amygdala nuclei.

TABLE 1

CTGF Expression Across Amygdala Nuclei

| Symbol | AAA | AB | AHA | Basal | Central | CO | Lateral | Medial | PAC | PL | Median P |
|---|---|---|---|---|---|---|---|---|---|---|---|
| CTGF | 0.0022 | 2.44E−11 | 4.92E−04 | 0.096 | 0.865 | 0.880 | 4.07E−04 | 0.041 | 0.804 | 0.228 | 0.069 |
| CTGF | 0.022 | 1.61E−08 | 1.24E−04 | 0.014 | 0.821 | 0.765 | 7.70E−04 | 0.117 | 0.381 | 0.344 | 0.069 |

Example 3. Altered Expression of CTGF Pathway Members in Low Anxiety Versus High Anxiety Animals This example illustrates that highly anxious rats (LRs) had higher CTGF expression (i.e., 1.95-fold) than less anxious rats (HRs) in the hippocampus. CTGF gene expression in the dentate gyrus was initially assessed by Illumina Rat Expression BeadChips and analyzed by BeadStudio. Microarray analysis showed significantly higher CTGF expression in the dentate gyrus of LRs compared to HRs. The probe sequence used for the microarray analysis was: 5'-CCACGAGGAAGTGTTTGCTGCTTCTTTGACTAT-GACTGGTTTGGGAGGCA-3' (SEQ ID NO:4). Following the microarray experiments, RT-PCR was performed using fresh RNA extracted from the whole hippocampus of LRs and HRs. Equal amounts of high quality RNA were loaded into the cDNA synthesis. The cDNA was then diluted 1:10 and used in PCR reactions. The PCR primers were previously validated using standard curves and melt-curves. The primer sequences were as follows: forward, 5'-AGAGTG-GAGATGCCAGGAGA-3' (SEQ ID NO:5); and reverse, 5'-CACACACCCAGCTCTTGCTA-3' (SEQ ID NO:6).

This example also illustrates that low anxiety animals treated with vehicle (HR-VEH) displayed significantly less CTGF expression (p<0.001) than high anxiety animals treated with vehicle (LR-VEH). See, Table 2. In addition, this example illustrates that high anxiety animals treated with a drug that reduces anxiety such as FGF2 (LR-FGF2) had significantly decreased CTGF expression (p<0.001) than high anxiety animals treated with vehicle (LR-VEH). See, Table 2. This example further illustrates that CTGF pathway members such as ECM2, EGR1, BCL2L2, IGFBP7, P4HA1, PDGFB, MAPKAPK5, MAPK8IP3, PKN1, PRKAG1, CREB1, RHOG, RHOA, SOX4, and STK3 were differentially expressed between LR-FGF2 vs. LR-VEH animals and HR-VEH vs. LR-VEH animals. See, Table 2. ECM2 was significantly upregulated in the amygdala of human individuals with major depressive disorder (MDD) relative to controls. RHOG was significantly downregulated in the amygdala of human individuals with MDD relative to controls.

TABLE 2

Expression of CTGF Pathway Members

| | LR-FGF2 vs. LR-VEH | HR-VEH vs. LR-VEH |
|---|---|---|
| CTGF | Down | Down |
| ECM2 | Down | — |
| EGR1 | Down | — |
| BCL2L2 | Down | Down |
| IGFBP7 | Down | Down |
| P4HA1 | Down | — |
| PDGFB | — | Down |
| MAPKAPK5 | — | Down |
| MAPK8IP3 | — | Down |
| PKN1 | — | Down |
| PRKAG1 | — | Down |
| Creb/CREB1 | Up | — |
| RHOG | — | Up |
| RHOA | Up | Up |
| SOX4 | Up | — |
| STK3 | Up | — |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for decreasing depression-like behavior in an individual in need thereof, the method comprising:
    (a) administering to the individual a therapeutically effective amount of a connective tissue growth factor (CTGF) inhibitor.

2. The method of claim 1, wherein the depression-like behavior is associated with a mood disorder, anxiety, or an anxiety disorder.

3. The method of claim 2, wherein the mood disorder is major depressive disorder or bipolar disorder.

4. The method of claim 1, wherein the CTGF inhibitor is selected from the group consisting of an antibody, an interfering RNA, a small molecule compound, and combinations thereof.

5. The method of claim 4, wherein the antibody is a human, humanized, or chimeric anti-CTGF monoclonal antibody or an antigen-binding fragment thereof.

6. The method of claim 5, wherein the human anti-CTGF monoclonal antibody is FG-3019.

7. The method of claim 1, wherein the CTGF inhibitor substantially relieves one or more symptoms of the depression-like behavior.

8. The method of claim 1, wherein the CTGF inhibitor is administered intravenously, intracranially, intracerebroventricularly, intrathecally, intraspinally, intraperitoneally, intramuscularly, intralesionally, intranasally, orally, or subcutaneously.

* * * * *